(12) United States Patent
Saito

(10) Patent No.: US 7,267,891 B2
(45) Date of Patent: Sep. 11, 2007

(54) COMPOUND FOR LIGHT EMITTING DEVICE AND ORGANIC LIGHT EMITTING DEVICE USING THE SAME

(75) Inventor: Kaori Saito, Moriguchi (JP)

(73) Assignee: Sanyo Electric Co., Ltd., Osaka (JP)

( * ) Notice: Subject to any disclaimer, the term of this patent is extended or adjusted under 35 U.S.C. 154(b) by 331 days.

(21) Appl. No.: 10/813,625

(22) Filed: Mar. 31, 2004

(65) Prior Publication Data

US 2005/0072970 A1    Apr. 7, 2005

(30) Foreign Application Priority Data

Mar. 31, 2003  (JP)  ............................. 2003-097303
Mar. 25, 2004  (JP)  ............................. 2004-088149

(51) Int. Cl.
*H01L 51/54* (2006.01)
*C09K 11/06* (2006.01)

(52) U.S. Cl. ...................... 428/690; 428/917; 313/504; 313/506; 257/E51.044; 546/4; 546/13

(58) Field of Classification Search .................... None
See application file for complete search history.

(56) References Cited

U.S. PATENT DOCUMENTS

| 2002/0193532 | A1* | 12/2002 | Ikehira et al. | ............ | 525/333.3 |
| 2005/0025995 | A1* | 2/2005 | Cheng et al. | ................ | 428/690 |
| 2005/0147843 | A1* | 7/2005 | Kobayashi et al. | .......... | 428/690 |
| 2005/0170202 | A1* | 8/2005 | Tamao et al. | ................ | 428/690 |
| 2006/0134459 | A1* | 6/2006 | Huo et al. | .................. | 428/690 |

FOREIGN PATENT DOCUMENTS

| JP | 2005-100881 A | * | 4/2005 |
| WO | WO 03/084973 A1 | * | 10/2003 |
| WO | WO 2004/003053 A1 | * | 1/2004 |

OTHER PUBLICATIONS

M.A. Baldo et al., "Very high-efficiency green organic light-emitting devices based on electrophosphorescence" Applied Physics Letters vol. 75, No. 1, p. 4, (1999).
J. AM. Chem. Soc., "Poly (p-phenylene-borane)s. Novel Organoboron π- Conjugated Polymers via Grignard Reagent" 120, 10776 (1998), Matsumi et al.
J. Am. Chem. Soc., "A Novel Class of emitting Amorphous Molecular Materials as Bipolar Radical Formants: 2-(4-[Bis(4-methylphenyl)amino]phenyl)-5-(dimesitylboryl)thiophene and 2-(4-[Bis(9,9-dimethylfluorenyl)amino]phenyl)-5-(dimesitylboryl)thiophene"122, 11021 (2000), Shirota et al.
S. Lamansky, et al, J. Am. Chem. Soc., "Highly Phosphorescent Bis-Cyclometalated Iridium Complexes: Synthesis, Photphysical Characterization, and Use in Organic Light Emitting Diodes" 123, 4304-4312 (2001).
C. Adachi et al, Appl. Phys. Lett., "Organic electroluminescent device having a hole conductor as an emitting layer" 55, 1489, (1989).
C. W. Tang et al, Appl. Phys. Lett., "Organic electroluminescent diodes" 1987, 51, 913, (1987).
S.A. Vanslyke et al, Appl. Phys. Lett., "Organic electroluminescent devices with improved stability" 69, 2160 (1996).

* cited by examiner

*Primary Examiner*—Marie Yamnitzky
(74) *Attorney, Agent, or Firm*—McDermott Will & Emery LLP

(57) ABSTRACT

An organic EL device according to the present invention has a layered structure in which a hole injection electrode (anode), a hole injection layer, a hole transport layer, a light emitting layer, a hole blocking layer, an electron injection layer, and an electron injection electrode (cathode) are layered in this order on a substrate. The light emitting layer is composed of a host material and an emitting dopant. A compound for light emitting device which is an organic material is employed for the emitting material. The compound for light emitting device is a metal complex employing a ligand having a substituent containing boron.

9 Claims, 7 Drawing Sheets

F I G. 1
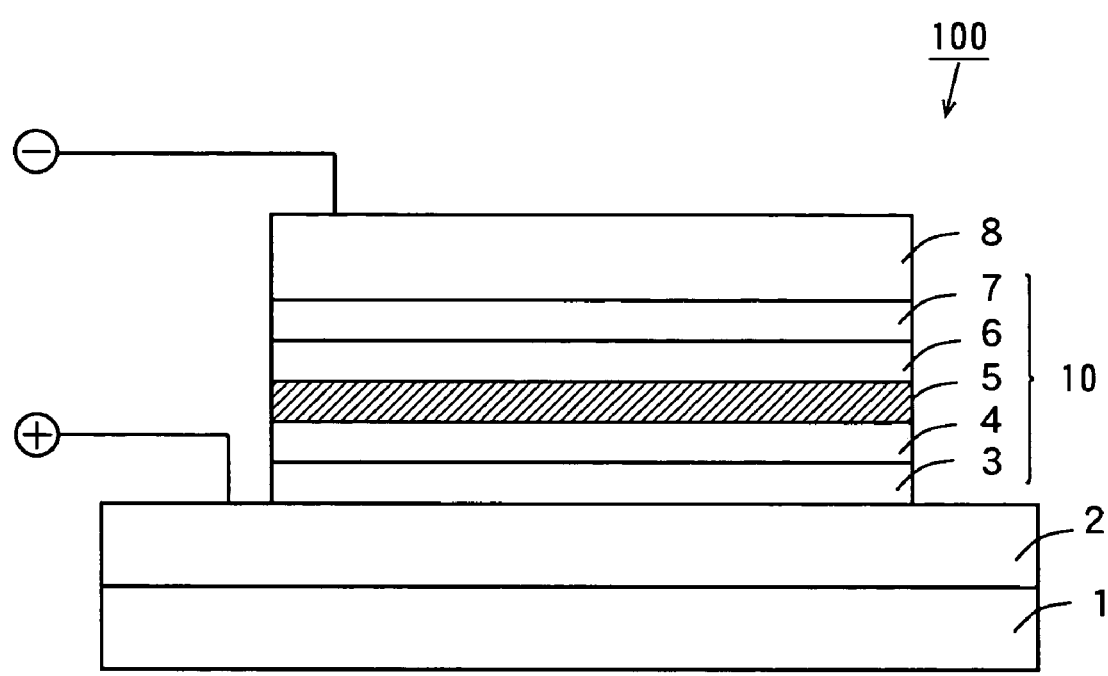

COMPOUND FOR LIGHT EMITTING DEVICE AND ORGANIC LIGHT EMITTING DEVICE USING THE SAME

BACKGROUND OF THE INVENTION

1. Field of the Invention

The present invention relates to a compound for light emitting device and an organic light emitting device using the same.

2. Description of the Background Art

The organic electroluminescent device (hereinafter abbreviated as an organic EL device) is expected as a new type self light emitting device. The organic EL device has a layered structure including a carrier transport layer (electron or hole transport layer) and a light emitting layer between a hole injection electrode and an electron injection electrode. An electrode material having a large work function such as gold (Au) or ITO (Indium-Tin Oxide) is used for the hole injection electrode, while an electrode material having a small work function such as Mg (magnesium) or Li (lithium) is used for the electron injection electrode.

An organic material is used for each of the hole transport layer, light emitting layer, and electron transport layer. A material having the characteristic of p-type semiconductor is used for the hole transport layer, while a material having the characteristic of n-type semiconductor is used for the electron transport layer. The light emitting layer also has carrier transport capability such as electron or hole transport capability, and is made of an organic material emitting fluorescent light or phosphorescent light.

The hole injection electrode, hole transport layer, light emitting layer, electron transport layer, and electron injection electrode are layered in this order to form a device. Note that depending upon organic materials to be used, these functional layers such as the hole transport layer, electron transport layer and light emitting layer may each include a plurality of layers or some of them may not be provided at all.

As examples of such device structures, there may be mentioned: a structure in which only two organic layers, the light emitting layer and electron transport layer exist between the hole injection electrode and electron injection electrode; a structure in which only two organic layers, the hole transport layer and light emitting layer exist; and a device structure in which only three organic layers, the hole injection layer, hole transport layer, and light emitting layer exist. The device structure may be adjusted according to the characteristics of the material used for each organic layer.

The organic EL device can provide a visible light ranging from blue to red by selecting an organic material forming the light emitting layer. Therefore, through the use of organic EL devices emitting respective monochromatic lights of red, green, and blue which are three primary colors of light (RGB), a full-color display is realized.

By the way, among the red, green, and blue lights obtained by the organic EL devices, green and blue lights are stable.

M. A. Baldo et al., for example, has reported that the employment of iridium(III)tris(2-phenylpyridinato)-N,C$^2$ (hereinafter abbreviated as Ir(ppy)3) led to the achievement of high efficient luminescent characteristics (see, M. A. Baldo et al., Applied Physics Letters, Vol. 75, No. 1, p4, (1999)). The molecular structure of Ir(ppy)3 is expressed in the following formula (4):

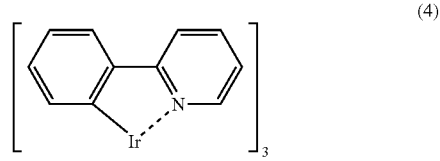

As expressed in the formula (4), Ir(ppy)3 is a complex of phenylpyridine and iridium metal, emitting green light.

On the other hand, it is difficult to obtain orange-red light having high luminance and luminous efficiency. This is because there is no solid organic material that effectively emits fluorescent or phosphorescent light of orange-red color.

With relation to the above, a method has been proposed in which the luminescent wavelength of an organic EL device is shifted to a longer wavelength in order to effectively obtain an orange-red emission.

There is, for example, a method in which a heterocyclic ring structure with a small energy gap is employed for a ligand of a complex forming an emitting material. As for this method, a case using an iridium complex having a ligand of a derivative, such as benzothiophene or benzothiazole as an emitting material, has been reported (see, S. Lamansky et al., J. Am. Chem. Soc., 123, 4304-4312 (2001)). Using this kind of emitting material, a maximum luminescent wavelength can be shifted to a longer wavelength.

Such an emission spectrum, however, has a broad shape than the emission spectrum of Ir(ppy)3 emitting green light. This may inhibit achievement of an emission color with good purity, causing the emission to extend out of a visible range (near infrared radiation range).

In addition, there is a method in which a ligand having a fused ring structure is employed for the complex forming a emitting material, so that the π conjugated system is extended to make an energy gap smaller. As for this method, a case using a complex having a ligand of a fused polycyclic compound, such as benzoquinoline or phenylquinoline as an emitting material, has been reported (refer to S. Lamansky et al., J. Am. Chem. Soc., 123, 4304-4312 (2001)). Using such emitting material, a maximum luminescent wavelength can be shifted to a longer wavelength.

However, in this case also, the emission spectrum results in a broader shape than the emission spectrum of Ir(ppy)3 emitting green light. As a result, light of high color purity is not obtained.

SUMMARY OF THE INVENTION

It is an object of the present invention is to provide a compound for light emitting device having excellent luminous efficiency while providing excellent color purity, and an organic light emitting device using the same.

In the case where a maximum luminescent wavelength is shifted to a longer wavelength, the emission spectrum results in a broad shape. When the emission spectrum is in a broad shape, an emission color of good purity is not obtained with the emission extending out of a visible range (near infrared range). Such a broad emission spectrum is accordingly considered to be one cause of the lowered luminous efficiency.

The present inventors presumed that, as for the emitting material emitting green, by the use of Ir(ppy)3 employing a ligand having a basic skeleton of phenylpyridine in which another substituent is directly introduced, it may become possible to attain a compound for light emitting device (emitting material) in which the maximum luminescent wavelength is shifted to a longer wavelength, with the shape of the emission spectrum of Ir(ppy)3 being maintained.

In a conventional iridium complex having a ligand in which a substituent of an alkyl group, such as a methyl group, an aryl group, an alkoxy group, a halogen group, or the like is substituted on phenylpyridine, it has not been possible to shift the luminescent wavelength from green to a longer wavelength.

For this reason, the present inventors repeatedly conducted various experiments and examinations, and as a result, reached to the idea of the compound for light emitting device according to the following invention.

A compound for light emitting device according to one aspect of the present invention has a molecular structure expressed by the following formula (1), where at least one out of R1 to R8 is a substituent containing boron; the others are each a hydrogen atom or a substituent; L is a ligand; M is a metal; m represents an integer from 0 to 4; n represents an integer from 1 to 3:

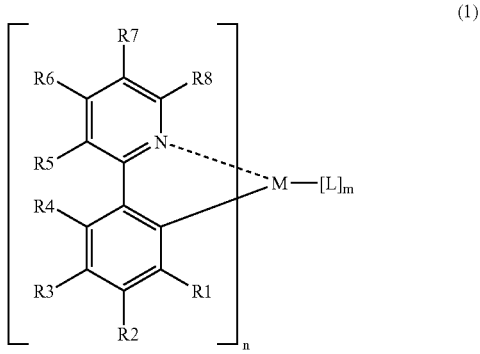

(1)

In the compound for light emitting device expressed by the above formula (1), the substituent may be expressed by the following formula (2), where R11 and R12 are identical to or different from each other, each being a hydrogen atom or a substituent:

(2)

In the substituent containing boron expressed by the above formula (2), the R11 and R12 may each be a mesityl group.

In the compound for light emitting device expressed by the above formula (1), L may be a ligand selected from the group consisting of a halogen ligand, a carboxylic acid ligand, an imine ligand, a nitrogen-containing heterocyclic ligand, a diketone ligand, a phosphorus ligand, an isocyanide ligand, an ortho carbometallation ligand, a hexafluorophosphine ligand, a cyclopentadienyl ligand, and a carbon monoxide ligand.

In the compound for light emitting device expressed by the above formula (1), L may be a ligand selected from the group consisting of a picolinic acid ligand, a salicylic acid ligand, a salicylimine ligand, an acetylacetone ligand, and an ortho carbometallation ligand.

In the compound for light emitting device expressed by the above formula (1), M may be a metal selected from the group consisting of iridium, platinum, palladium, rhodium, and rhenium.

In the compound for light emitting device expressed by the above formula (1), the R1 and R3 to R8 may each be a hydrogen atom.

In the compound for light emitting device having such a molecular structure, the metal complex which has high-efficient luminescent characteristics and is relatively stable is employed, while as a ligand for the metal complex, the ligand into which the substituent containing boron is introduced is employed. This prevents the emission spectrum from spreading over a wide range, thereby attaining excellent color purity. Furthermore, an emission in which the maximum luminescent wavelength is shifted to a longer wavelength is attained.

In addition, with the introduction of the substituent containing boron into the ligand employed in the metal complex, the emission color can be varied, and improved electron transport capability is also attained. This results in excellent luminous efficiency.

An organic light emitting device according to another aspect of the present invention comprises a hole injection electrode; an electron injection electrode; a light emitting layer provided between the hole injection electrode and the electron injection electrode, the light emitting layer contains an organic compound having a molecular structure expressed by the following formula (1), where at least one out of R1 to R8 is a substituent containing boron; the others are each a hydrogen atom or a substituent; L is a ligand; M is a metal; m represents an integer from 0 to 4; and n represents an integer from 1 to 3:

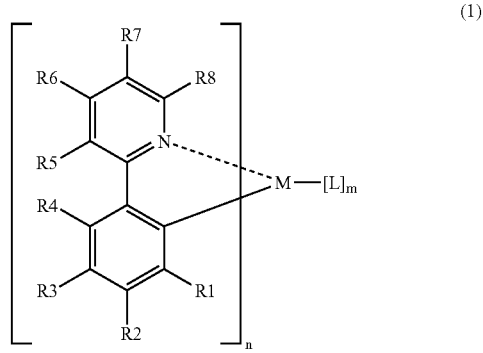

(1)

In the organic light emitting device, the compound for light emitting device having the molecular structure expressed by the above formula (1) is employed. In this compound for light emitting device, the metal complex which has high-efficient luminescent characteristics and is relatively stable is employed, while as a ligand for the metal complex, the ligand into which the substituent containing boron is introduced is employed. This prevents the emission spectrum from spreading over a wide range, thereby attaining excellent color purity. Furthermore, an emission in which the maximum luminescent wavelength is shifted to a longer wavelength is attained.

In addition, with the introduction of the substituent containing boron into the ligand employed in the metal complex, the emission color can be varied, and electron transport capability is also improved. This results in excellent luminous efficiency.

The organic light emitting device having the compound for light emitting device of the molecular structure expressed by the above formula (1), can provide excellent color purity and luminous efficiency.

The light emitting layer may contain a host material and the organic compound expressed by the formula (1), the content of the organic compound being not less than 0.1% nor more than 30% by weight for the host material. This results in a satisfactory emission from the compound for light emitting device.

The host material may be 4,4'-N,N'-dicarbazole-1,1'-biphenyl having a molecular structure expressed by the following formula (3):

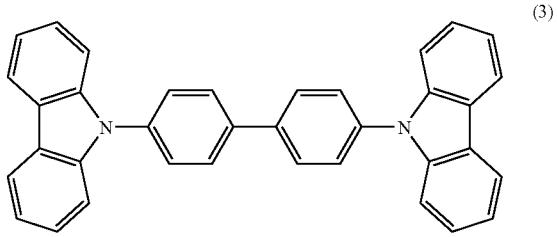

(3)

An organic light emitting device according to still another aspect of the present invention comprises a hole injection electrode; an electron injection electrode; a carrier transport layer provided between the hole injection electrode and the electron injection electrode; and a light emitting layer provided between the hole injection electrode and the electron injection electrode, at least one of the carrier transport layer and the light emitting layer contains an organic compound having a molecular structure expressed by the following formula (1), where at least one out of R1 to R8 is a substituent containing boron; the others are each a hydrogen atom or a substituent; L is a ligand; M is a metal; m represents an integer from 0 to 4; and n represents an integer from 1 to 3:

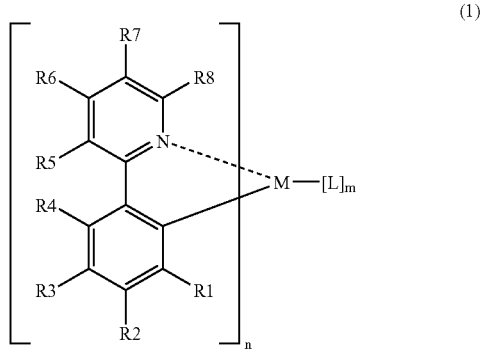

(1)

In the organic light emitting device, the compound for light emitting device having the molecular structure expressed by the above formula (1) is employed. In this compound for light emitting device, the metal complex which has high-efficient luminescent characteristics and is relatively stable is employed, while as a ligand for the metal complex, the ligand into which the substituent containing boron is introduced is employed. This prevents the emission spectrum from spreading over a wide range, thereby attaining excellent color purity. Furthermore, an emission in which the maximum luminescent wavelength is shifted to a longer wavelength is attained.

In addition, with the introduction of the substituent containing boron into the ligand employed in the metal complex, the emission color can be varied, and electron transport capability is also improved. This results in excellent luminous efficiency.

The organic light emitting device having the compound for light emitting device of the molecular structure expressed by the above formula (1), can provide excellent color purity and luminous efficiency.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a schematic cross-sectional view showing one example of an organic EL device according to a first embodiment;

DESCRIPTION OF THE PREFERRED EMBODIMENTS

Figure 2:
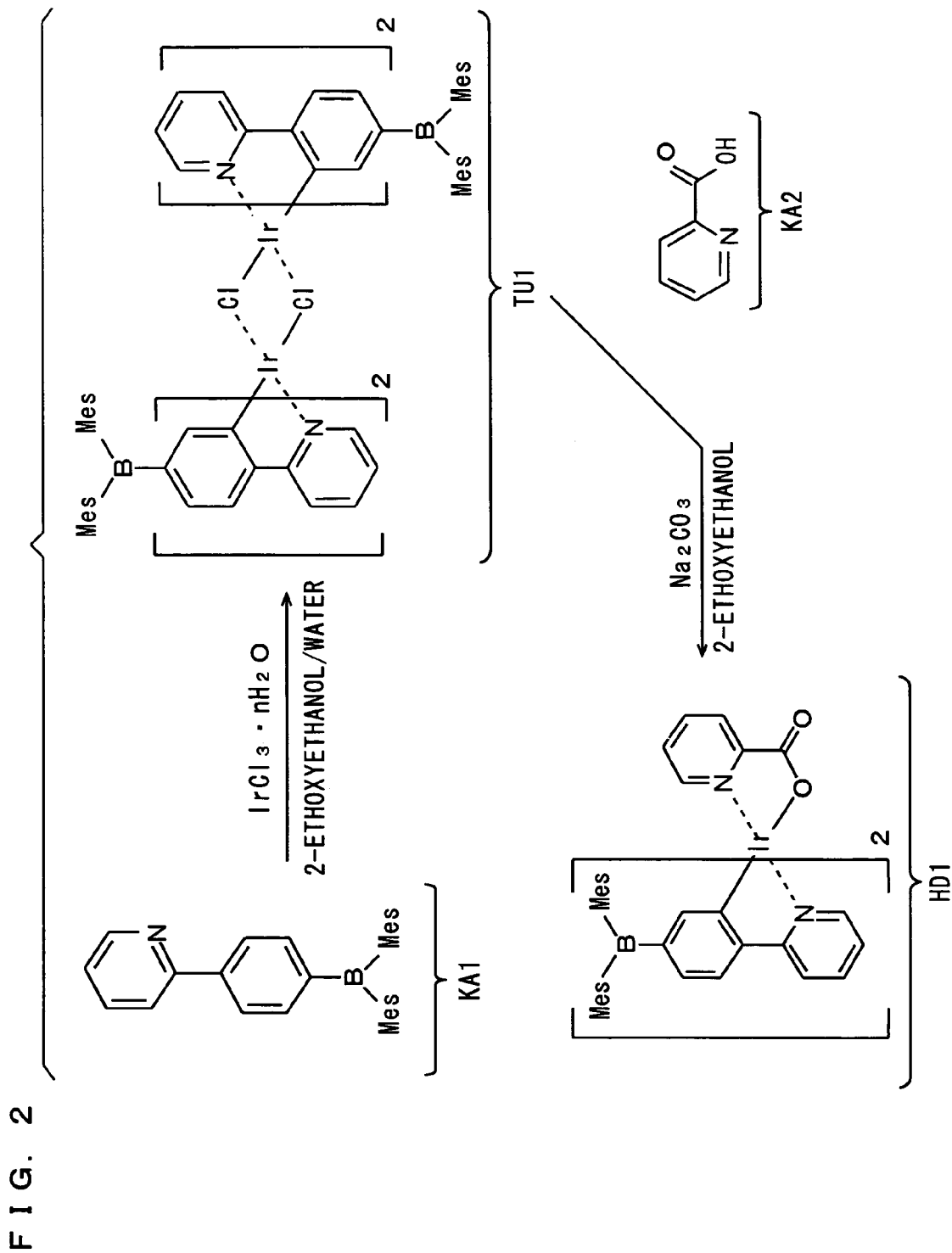
FIG. 2 is a schematic diagram showing one example of a process of preparing the compound for light emitting device according to the first embodiment.

Description will, hereinafter, be made of a compound for light emitting device according to an embodiment of the present invention, and a light emitting device using the same. A light emitting device in the following represents an organic electroluminescent (hereinafter abbreviated as EL) device.

First Embodiment

FIG. 1 is a schematic cross-sectional view showing one example of an organic EL device according to a first embodiment. An organic EL device 100 according to the first embodiment has a layered structure including a hole injection electrode 2 (anode), an organic compound layer 10, and an electron injection electrode 8 (cathode) in this order on a glass substrate 1. The organic compound layer 10 is formed of a hole injection layer 3, a hole transport layer 4, a light emitting layer 5, a hole blocking layer 6, and an electron injection layer 7.

The substrate 1 is a transparent substrate composed of glass, plastic, or the like. The hole injection electrode 2 is a transparent or semi-transparent electrode composed of a metal compound such as indium-tin oxide (hereinafter abbreviated as ITO), a metal such as silver, or an alloy. The electron injection electrode 8 is a transparent, semi-transparent, or non-transparent electrode composed of a metal compound such as magnesium-indium alloy or ITO, a metal such as magnesium (Mg) or lithium (Li), or an alloy.

In the organic compound layer 10, the hole injection layer 3 is composed of an organic material, such as copper phthalocyanine (hereinafter abbreviated as CuPc) expressed by the following formula (5):

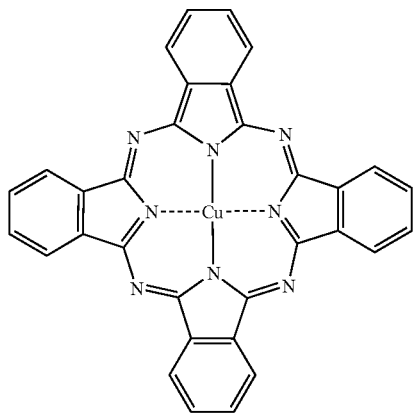
(5)

The hole transport layer 4 is composed of an organic material, such as N,N'-Di(naphthalene-1-yl)-N,N'-diphenyl-benzidine (hereinafter abbreviated as NPB) expressed by the following formula (6):

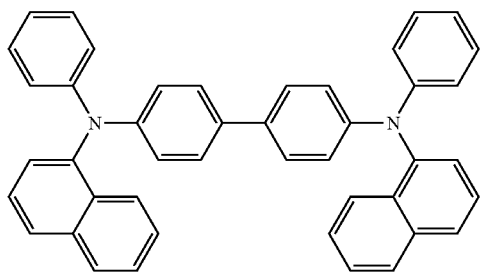
(6)

The light emitting layer 5 is composed of a host material and an emitting dopant as shown below. Each type of organic materials to be employed for the light emitting layer 5 will later be described.

The hole blocking layer 6 is composed of an organic material, such as 2,9-dimethyl-4,7-diphenyl-1,10-phenanthroline (hereinafter abbreviated as BCP) expressed by the following formula (7) or ((1,1'-bisphenyl)-4-olato)(2-methyl-8-quinolinolato-N1,08)aluminum expressed by the following formula (8):

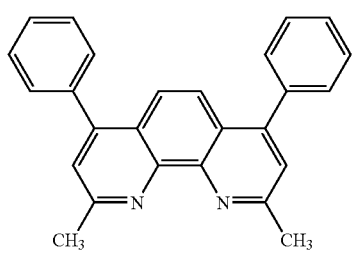
(7)

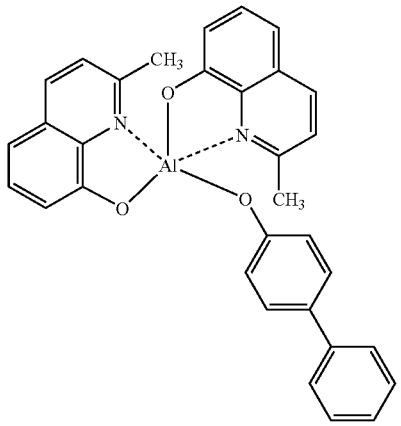
(8)

The electron injection layer 7 is composed of an organic material, such as Tris(8-hydroxyquinolinato)aluminum (hereinafter abbreviated as Alq) expressed by the following formula (9):

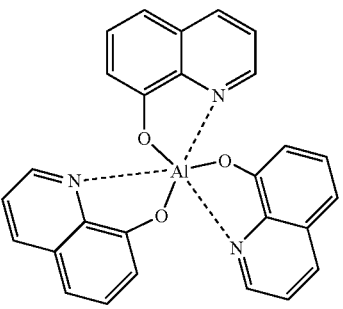
(9)

When voltage is applied between the hole injection electrode 2 and the electron injection electrode 8 in the organic EL device 100, the light emitting layer 5 emits light. The light produced in the light emitting layer 5 is emitted outside through the hole transport layer 4, hole injection layer 3, hole injection electrode 2, and substrate 1. Such a device structure in which the light produced in the light emitting layer 5 is emitted outside through the substrate 1 will be called "a back-emission structure".

Description will now be made of organic materials employed for the light emitting layer 5. As a host material of the light emitting layer 5, an organic material, such as 4,4'-bis(carbazole-9-yl)-biphenyl (hereinafter abbreviated as CBP) expressed by the following formula (3) is employed:

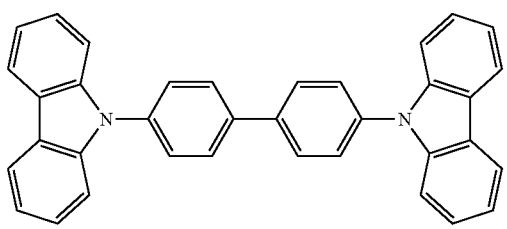
(3)

As an emitting dopant of the light emitting layer 5, a compound for light emitting device made of an organic material is employed. The compound for light emitting device has a molecular structure expressed by the following formula (1):

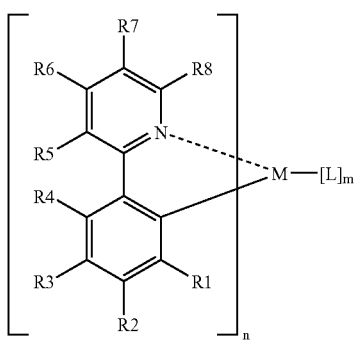

(1)

where at least one out of R1 to R8 is a substituent containing boron. The remainder are each any of a hydrogen atom or a substituted or unsubstituted, alkyl group (carbon number of 1-20), alkenyl group (carbon number of 2-25), alkynyl group, alkoxy group, aryl group, aralkyl group, aryloxy group, arylthio group, heterocyclic group, amino group, acyl group, alkoxycarbonyl group, aryloxycarbonyl group, acyloxy group, acylamino group, hydroxyl group, imino group, cyano group, nitro group, halogen group, sulfonyl group, or silyl group.

The alkyl group represented by any of R1 to R8 may be an alkyl group having the arrangement of carbon including branched-chain or cyclic-chain as well as straight-chain. As an example of such alkyl group, there may be mentioned: a methyl group, an ethyl group, a propyl group, an isopropyl group, an n-butyl group, a t-butyl group, a cyclohexyl group, a cyclopentyl group, an n-octadecyl group, or an n-dodecyl group. Among the alkyl groups represented by any of R1 to R8, the cyclohexyl group or the t-butyl group, i.e., a straight-chain alkyl group at carbon number 1 to 10, is preferable.

As the alkenyl group represented by any of R1 to R8, a phenylalkenyl group, a diphenyl alkenyl group, or a triphenylalkenyl group in which at least one substituent is a phenyl group is preferable. An unsubstituted alkenyl group may also be employed.

The aryl group represented by any of R1 to R8 may be either monocyclic or polycyclic, including a fused ring or a ring assembly. The aryl group is preferably has a carbon number of 6 to 30 in total, and may additionally has a substituent. As an example of such aryl group, there may be mentioned: a phenyl group, a (o-, m-, p-)tolyl group, a (o-, m-, p-)biphenyl group, a (o-, m-, p-)N-substituted anilino group, a fluoryl group, a terphenyl group, a (1-, and 2-)naphtyl group, an anthryl group, a pyrenyl group, a perylenyl group, and a phenanthryl group.

As an example of the acyl group represented by any of R1 to R8, there may be mentioned: an acetyl group, a benzoyl group, a pivaloyl group, and a formyl group.

The above-mentioned substituent containing boron has a molecular structure expressed by the following formula (2):

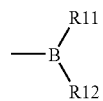

(2)

where each of R11 and R12 is a hydrogen atom or a substituent. As an example of the substituent, there may be mentioned: an unsubstituted or substituted, alkyl group, alkenyl group, alkoxy group, aryl group, fused ring group at a ring number of 2 to 4, heterocyclic group, and aryloxy group. R11 and R12 may be bonded with each other to form a ring.

It is preferable that R11 and R12 are both branched-chain alkyl groups at carbon number 3 to 10 or aryl groups substituted with alkyl groups, and more preferable that R11 and R12 are both isopropyl groups, t-butyl groups, phenethyl groups, thexyl groups, (o-, m-, p-)tolyl groups, mesityl groups, tripyl groups, or anthranyl groups.

In the formula (1), L represents a ligand. The ligand may be a polydentate ligand such as a bidentate ligand, other than a monodentate ligand. Any ligand which can form a metal complex may be employed without particular limitation.

As an example of the above-described ligand, there may be mentioned: a halogen ligand, such as a chlorine ligand; a carboxylic acid ligand, such as a picolinic acid ligand or a salicylic acid ligand; an imine ligand, such as an N-substituted salicylimine ligand; a nitrogen-containing heterocyclic ligand, such as a phenanthroline ligand or a bipyridyl ligand; a diketone ligand, such as an acetylacetone ligand, a dibenzoylmethane ligand, or a ethyl malonate ligand; a phosphorus ligand, such as a triphenylphosphine ligand, a tributylphosphine ligand, or a trimethylphosphate ligand; an isocyanide ligand, such as a t-butylisocyanide ligand; an ortho carbometallation ligand, such as a phenylpyridine ligand; a hexafluorophosphine ($PF_6$) ligand; a cyclopentadienyl ligand; or a carbon monoxide ligand.

It is preferable that the ligand expressed by L in the formula (1) is a diketone ligand or a carboxylic acid ligand. It is more preferable that the ligand is an acetylacetone ligand among diketone ligands, still more preferable that it is a picolinic acid ligand among carboxylic acid ligands.

In the case where there are a plurality of ligands expressed by L shown in the formula (1), the ligands may be any of various types, and may belong to one type or two or more types, while it is preferable that the ligands belong to one type.

In the formula (1), M represents any metal out of iridium (Ir), platinum (Pt), palladium (Pd), rhodium (Rh), and rhenium (Re). Of these metals, M is preferably iridium, platinum or rhenium, more preferably, iridium.

The valence of the above-described metal is not limited, in particular; however, in the case where M is any of iridium, rhodium, and rhenium, M is preferably trivalent, and where M is platinum or palladium, M is preferably bivalent. In the formula (1), m represents an integer of 0 to 4, and n represents an integer of 1 to 3.

The compound for light emitting device (metal ligand compound) in accordance with the formula (1) having such a molecular structure may be a neutral complex or an ionic complex having counter salt, while a neutral complex is more preferable.

The compound for light emitting device according to the present embodiment is prepared, for example, as follows. FIG. 2 is a schematic diagram showing one example of a process of preparing the compound for light emitting device according to the first embodiment. The sign Mes shown in FIG. 2 represents a mesityl group, which is expressed by the following formula (10). In the following, the sign Mes shown in each of the formulas (11), (12), (14) represents a mesityl group expressed by the following formula (10):

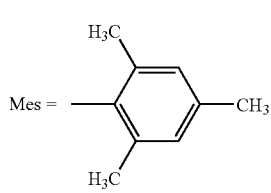

(10)

In a three-neck flask with a reflux tube, [4-(dimesitylboryl)phenyl]pyridine KA1 expressed by the following formula (11), iridium trichloride(III) n hydrate ($IrCl_3 \cdot nH_2O$), 2-ethoxyethanol, and water are mixed. Then, the mixture is stirred under reflux in a nitrogen atmosphere for 24 hours. A resultant reactance is cooled to the room temperature, and subsequently a precipitated solid is filtered. The filtered solid is washed in water and ethanol, and dried under reduced pressure to give yellow powder of a compound TU1 expressed by the following formula (12):

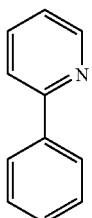

(11)

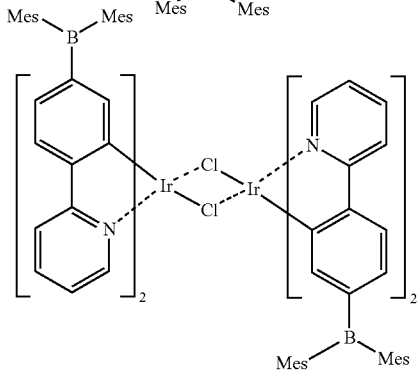

(12)

After that, in a three-neck flask with a reflux tube, the compound TU1, a picoline acid KA2 expressed by the following formula (13), 2-ethoxyethanol, and sodium carbonate ($Na_2CO_3$) are mixed. Then, the mixture is stirred under reflux in a nitrogen atmosphere for 15 hours. A resultant reactance is cooled to the room temperature, and subsequently a precipitated solid is filtered. The filtered solid is washed in water and ethanol, dried under reduced pressure, and purified using silica gel column chromatography (eluting solvent: dichloromethane) to give yellow powder of a compound HD1 for light emitting device expressed by the following formula (14):

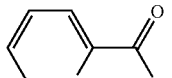

(13)

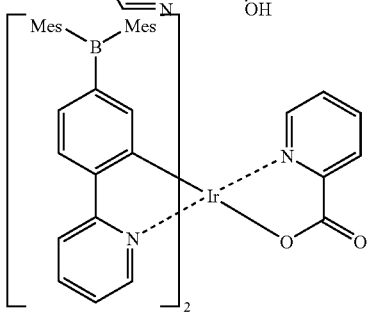

(14)

In the compound HD1 for light emitting device used in the present embodiment, a metal complex, such as an iridium complex having high efficient luminescent characteristics and is relatively stable is employed, while as a ligand to be employed in the metal complex, a ligand having a basic skeleton of phenylpyridine into which a substituent containing boron is introduced is employed.

This prevents the emission spectrum from spreading over a wide range, thereby attaining an emission in which a maximum luminescent wavelength is shifted to a longer wavelength. The compound HD1 for light emitting device provides an orange-red emission.

By the way, boron has a vacant p-orbital because it has one less electron than carbon. Nakajo et al., for example, has reported in "J. Am. Chem. Soc., 1998, 120, 10776, etc." that the introduction of boron atoms into the π conjugated system leads to extension of the π conjugated system via the vacant p-orbital.

Boron, which is an atom lacking in the number of electrons, has the affinity for electrons. Shirota et al., for example, has reported in "J. Am. Chem. Soc., 2000, 122, 11021., etc." that the introduction of boron can lead to improvement in transport capability of a material.

As can be seen from these reports, with the introduction of the substituent containing boron into the compound for light emitting device according to the present embodiment, the emission color can be varied, while electron transport capability is improved. This has led to reduced voltage and high efficiency of the light emitting device itself.

Thus, the organic EL device 100 according to the present embodiment provides excellent color purity and luminous efficiency.

Second Embodiment

An organic EL device according to a second embodiment has a similar structure as that of the organic EL device in the first embodiment except for the following points.

Figure 3:
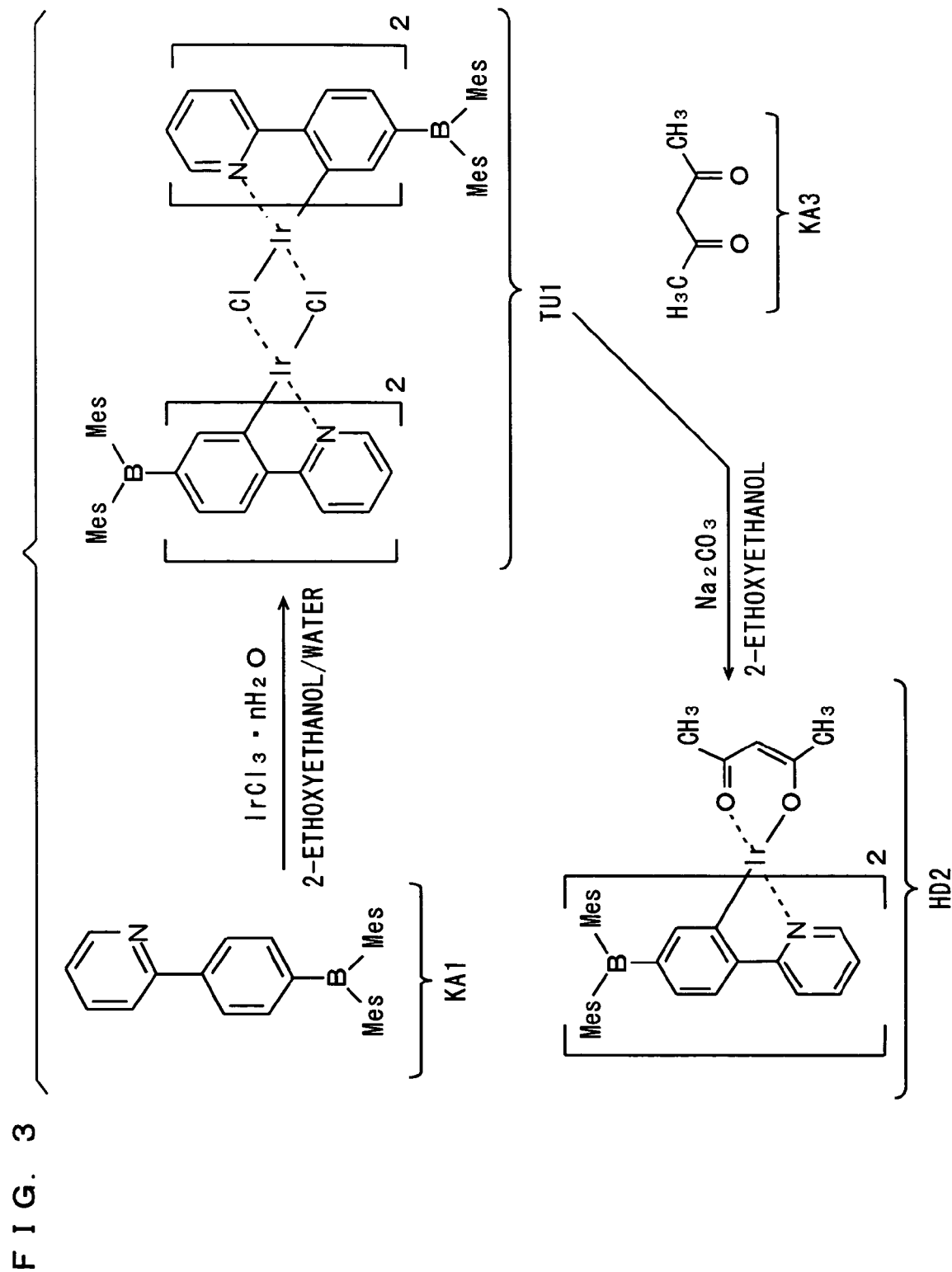
FIG. 3 is a schematic diagram showing one example of a process of preparing the compound for light emitting device according to the second embodiment.

In the present embodiment, a compound for light emitting device employed in the light emitting layer 5 is prepared, for example, as follows. FIG. 3 is a schematic diagram showing one example of a process of preparing the compound for light emitting device according to the second embodiment. The sign Mes shown in FIG. 3 represents a mesityl group expressed by the formula (10) above. In the following description, the sign Mes shown in the formula (16) represents a mesityl group expressed by the formula (10) above.

The compound TU1 prepared in the first embodiment is employed for the preparation of the compound for light emitting device according to the second embodiment. The compound TU1 is prepared in a similar process as applied in the first embodiment.

In a three-neck flask with a reflux tube, the compound TU1, acetylacetonate KA3 expressed by the following formula (15), 2-ethoxyethanol, and sodium carbonate ($Na_2CO_3$) are mixed. Then, the mixture is stirred under reflux in a nitrogen atmosphere for 15 hours. A resultant reactance is cooled to the room temperature, and subsequently a precipitated solid is filtered. The filtered solid is washed in water and ethanol, dried under reduced pressure, and purified using silica gel column chromatography (eluting solvent: dichloromethane) to give yellow powder of a compound HD2 for light emitting device expressed by the following formula (16):

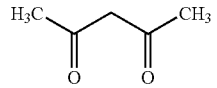

(15)

-continued

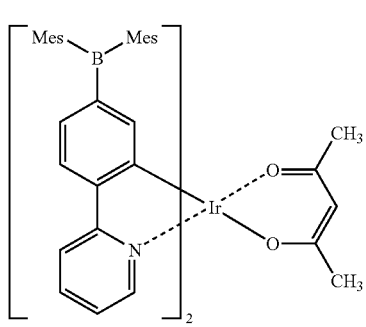

(16)

In the compound HD2 for light emitting device according to the present embodiment, a ligand into which a substituent containing boron is introduced is employed. This prevents the emission spectrum from spreading over a wide range, thereby attaining an emission in which a maximum luminescent wavelength is shifted to a longer wavelength. The compound HD2 for light emitting device provides an orange-red emission.

Moreover, because of the introduction of the substituent containing boron, the electron transport capability is improved, while the emission color can be varied. This has led to reduced voltage and high efficiency of the light emitting device itself.

Third Embodiment

An organic EL device according to a third embodiment has a similar structure as that of the organic EL device in the first embodiment except for the following points.

Figure 4:
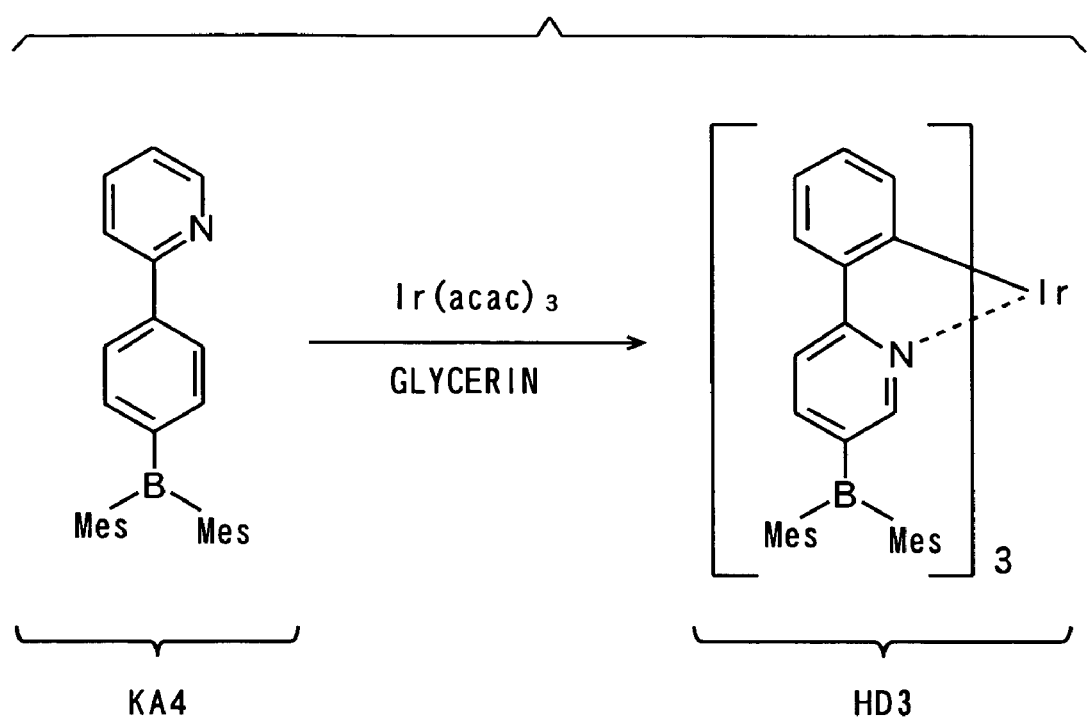
FIG. 4 is a schematic diagram showing one example of a process of preparing the compound for light emitting device according to the third embodiment.

In the present embodiment, a compound for light emitting device to be employed in the light emitting layer 5 is prepared, for example, as follows. FIG. 4 is a schematic diagram showing one example of a process of preparing the compound for light emitting device according to the third embodiment. The sign Mes shown in FIG. 4 represents a mesityl group expressed by the formula (10) above. In the following description, the sign Mes shown in each of the formulas (17), (18) represents a mesityl group expressed by the formula (10) above.

In a three-neck flask with a reflux tube, glycerol is heated to 140 to 150° C. and $N_2$-bubbled for an hour, and then cooled to the room temperature. After that, 2-[(4-(dimesitylboryl)phenyl)pyridine KA4 expressed by the following formula (17) and iridium(III)acetylacetonate (Ir(acac)$_3$) are added to the glycerol. The mixture is then stirred under reflux in a nitrogen atmosphere for 5 hours. A resultant reactance is cooled to the room temperature, and subsequently a precipitated solid is filtered. The filtered solid is washed in water and methanol, dried under reduced pressure, and then purified using silica gel column chromatography (eluting solvent: dichloromethane) to give yellow powder of a compound HD3 for light emitting device expressed by the following formula (18):

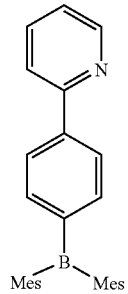

(17)

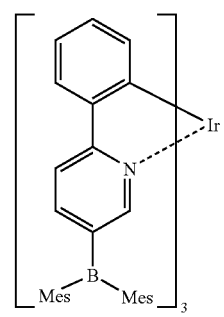

(18)

In the compound HD3 for light emitting device according to the present embodiment, a ligand in which a substituent containing boron is introduced is employed. This prevents the emission spectrum from spreading over a wide range, thereby attaining an emission in which a maximum luminescent wavelength is shifted to a longer wavelength. The compound HD3 for light emitting device provides an orange-red emission.

Moreover, because of the introduction of the substituent containing boron, the electron transport capability is improved, while the emission color can be varied. This has led to reduced voltage and high efficiency of the light emitting device itself.

Fourth Embodiment

An organic EL device according to a fourth embodiment has a similar structure as that of the organic EL device in the first embodiment except for the following points.

Figure 5:
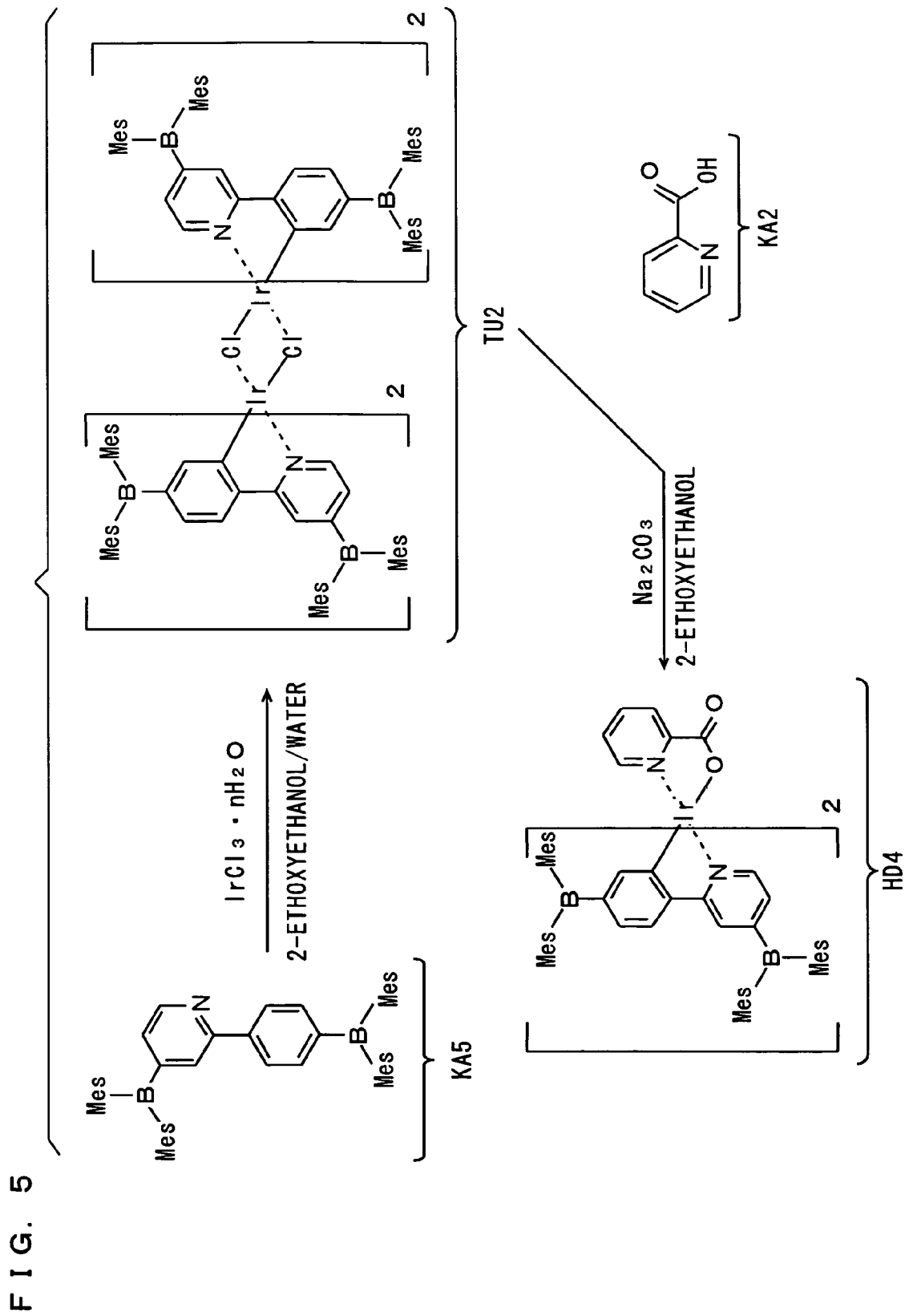
FIG. 5 is a schematic diagram showing one example of a process of preparing the compound for light emitting device according to the fourth embodiment.

In the present embodiment, a compound for light emitting device to be employed in the light emitting layer 5 is prepared, for example, as follows. FIG. 5 is a schematic diagram showing one example of a process of preparing the compound for light emitting device according to the fourth embodiment. The sign Mes shown in FIG. 5 represents a mesityl group expressed by the formula (10) above. In the following description, the sign Mes shown in each of the formulas (19), (20), (21) represents a mesityl group expressed by the formula (10) above.

In a three-neck flask with a reflux tube, 4-(dimesitylboryl)-2-[(4-(dimesitylboryl)phenyl)pyridine KA5 expressed by the following formula (19), iridium trichloride(III)n-hydrate (IrCl$_3$.nH$_2$O), 2-ethoxyethanol, and water are mixed. The mixture is then stirred under reflux in a nitrogen atmosphere for 20 hours. A resultant reactance is cooled to the room temperature, and subsequently a precipitated solid is filtered. The filtered solid is washed in water and ethanol, and dried under reduced pressure to give yellow powder of a compound TU2 for light emitting device expressed by the following formula (20).

After that, the compound TU2, a picolinic acid KA2 expressed by the formula (13) above, 2-ethoxyethanol, and sodium carbonate (Na$_2$CO$_3$) are mixed. The mixture is then stirred under reflux in a nitrogen atmosphere for 12 hours. A resultant reactance is cooled to the room temperature, and subsequently a precipitated solid is filtered. The filtered solid is washed in water and ethanol, dried under reduced pressure, and then purified using silica gel column chromatography (eluting solvent: dichloromethane) to give yellow powder of a compound HD4 for light emitting device expressed by the following formula (21):

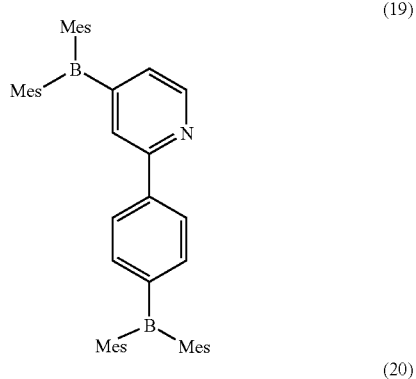

(19)

(20)

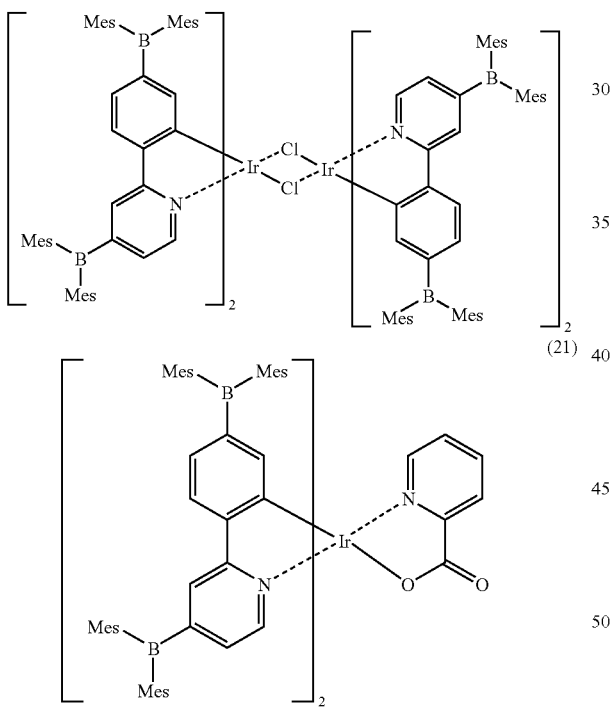

(21)

In the compound HD4 for light emitting device according to the present embodiment, a ligand in which a substituent containing boron is introduced is employed. This prevents the emission spectrum from spreading over a wide range, thereby attaining an emission in which a maximum luminescent wavelength is shifted to a longer wavelength. The compound HD4 for light emitting device provides an orange-red emission.

Moreover, because of the introduction of the substituent containing boron, the electron transport capability is improved, while the emission color can be varied. This has led to reduced voltage and high efficiency of the light emitting device itself.

Fifth Embodiment

An organic EL device according to a fifth embodiment has a similar structure as that of the organic EL device in the first embodiment except for the following points.

Figure 6:
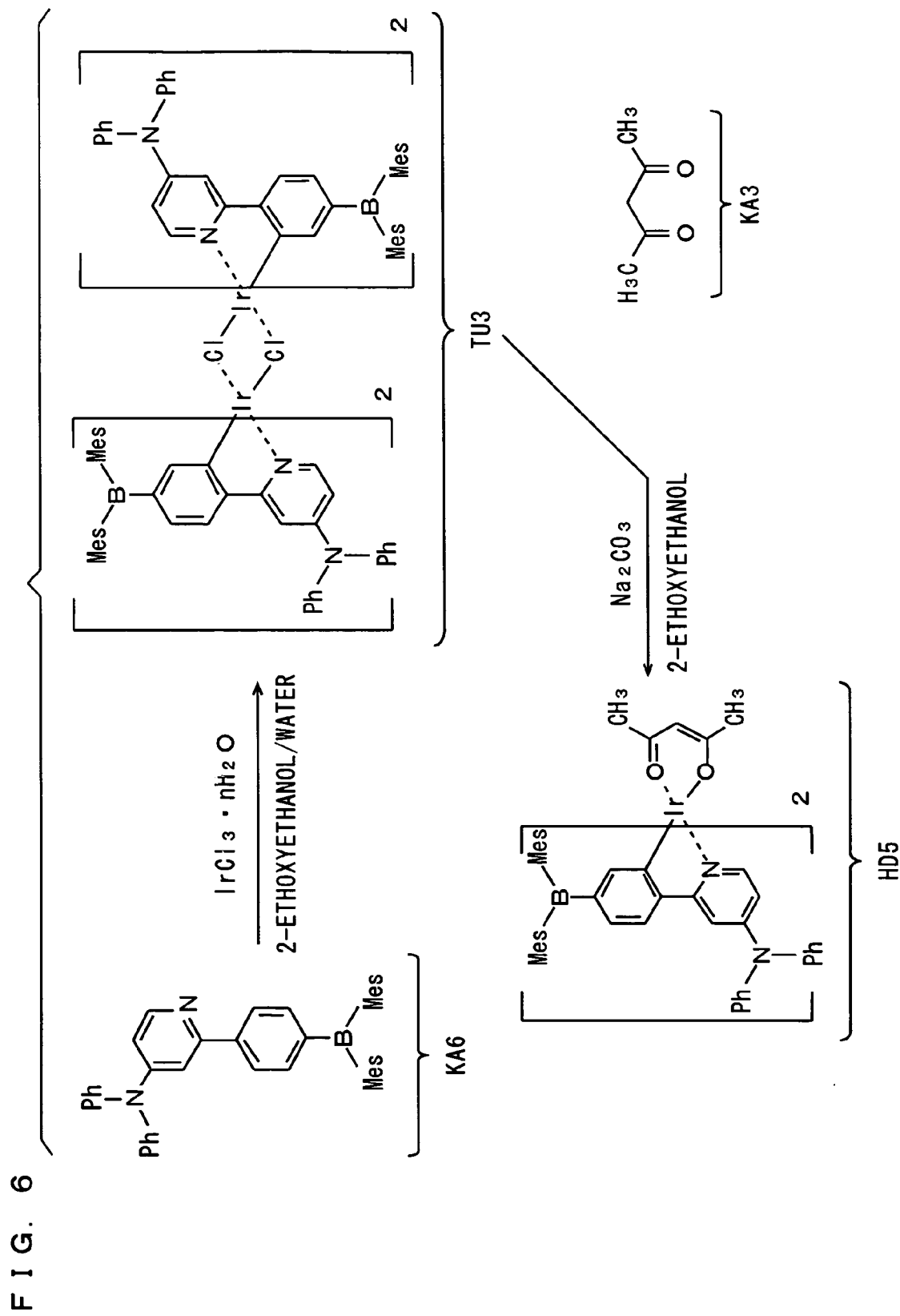
FIG. 6 is a schematic diagram showing one example of a process of preparing the compound for light emitting device according to the fifth embodiment.

In the present embodiment, a compound for light emitting device to be employed in the light emitting layer 5 is prepared, for example, as follows. FIG. 6 is a schematic diagram showing one example of a process of preparing the compound for light emitting device according to the fifth embodiment. The sign Mes shown in FIG. 6 represents a mesityl group expressed by the formula (10) above. In the following description, the sign Mes shown in each of the formulas (22), (23), (24) represents a mesityl group expressed by the formula (10) above.

In a three-neck flask with a reflux tube, 4-(dimesitylboryl)-2-[4-(N,N'-diphenylamino)phenyl]pyridine KA6 expressed by the following formula (22), iridium trichloride (III)n hydrate (IrCl$_3$.nH$_2$O), 2-ethoxyethanol, and water are mixed. The mixture is then stirred under reflux in a nitrogen atmosphere for 24 hours. A resultant reactance is cooled to the room temperature, and subsequently a precipitated solid is filtered. The filtered solid is washed in water and ethanol, and dried under reduced pressure to give yellow powder of a compound TU3 for light emitting device expressed by the following formula (23).

After that, in a three-neck flask with a reflux tube, the compound TU3, acetylacetonate KA3 expressed by the formula (15) above, 2-ethoxyethanol, and sodium carbonate (Na$_2$CO$_3$) are mixed. A resultant mixture is then stirred under reflux in a nitrogen atmosphere for 15 hours. A resultant reactance is cooled to the room temperature, and subsequently a precipitated solid is filtered. The filtered solid is washed in water and ethanol, dried under reduced pressure, and then purified using silica gel column chromatography (eluting solvent: dichloromethane) to give yellowish orange powder of a compound HD5 for light emitting device expressed by the following formula (24):

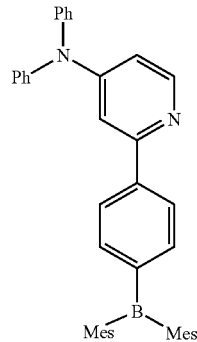

(22)

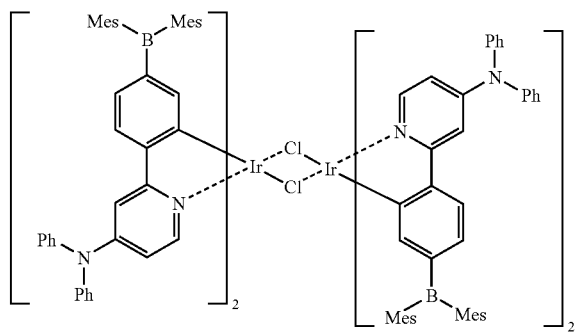

(23)

-continued

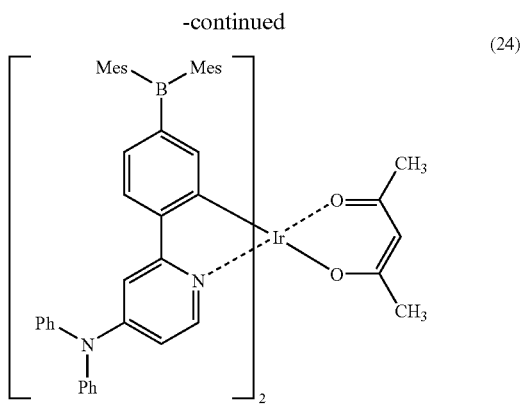
(24)

In the compound HD5 for light emitting device according to the present embodiment, a ligand into which a substituent containing boron is introduced is employed. This prevents the emission spectrum from spreading over a wide range, thereby attaining an emission in which a maximum luminescent wavelength is shifted to a longer wavelength. The compound HD5 for light emitting device provides an orange-red emission.

Moreover, because of the introduction of the substituent containing boron, the electron transport capability is improved, while the emission color can be varied. This has led to reduced voltage and high efficiency of the light emitting device itself.

In the first to fifth embodiments, it is desirable that the amount of the compound for light emitting device (emitting dopant) to be doped into the light emitting layer 5 is in a predetermined range. This is because doping of an excessive amount of the emitting dopant may, in same cases, cause lowering of the luminous intensity, luminous efficiency, and the like.

Specifically, it is preferable that the amount of the compound for light emitting device to be doped into the light emitting layer 5 is not less than 0.1% nor more than 30% by weight for the light emitting layer 5. This results in a satisfactory emission from the compound for light emitting device.

The organic EL device may have a top emission structure in which the light produced in the light emitting layer 5 is emitted through the hole blocking layer 6, electron injection layer 7, and electron injection electrode 8, with the electron injection electrode 8 being made of a transparent or semi-transparent electrode.

The light emitting layer 5 may be formed of two light emitting layers emitting different colors, respectively. For instance, when one of the two layers is doped with the compound for light emitting device according to any of the first to fifth embodiments that provides an orange-red emission, while the other is doped with a compound for light emitting device that provides a blue emission, a white light-emitting device is obtained. In this case, the use of the white light emitting device in combination with filters of red, green, and blue enables three primary colors of light (RGB display), thereby realizing a full-color display.

The organic EL device prepared according to any of the first to fifth embodiments that provides an orange-red emission may be used in combination with an organic EL device emitting green light and an organic EL device emitting blue light. In this case, the use of the organic EL device prepared according to any of the first to fifth embodiments as a pixel emitting red light (R pixel), an organic EL device emitting green light as a pixel emitting green light (G pixel), and an organic EL device emitting blue light as a pixel emitting blue light (B pixel) enables display of three primary colors of light (RGB display), thereby realizing a full-color display.

In the organic EL device according to each of the first to fifth embodiments, the organic EL device 100 corresponds to an organic light emitting device; the hole injection electrode 2 corresponds to a hole injection electrode; the electron injection electrode 8 corresponds to an electron injection electrode; the hole injection layer 3, hole transport layer 4, hole blocking layer 6, and electron injection layer 7 correspond to carrier transport layers; and the light emitting layer 5 corresponds to a light emitting layer.

Sixth Embodiment

An organic EL device according to a sixth embodiment has a similar structure as that of the organic EL device according to the first embodiment except that the light emitting layer 5 is composed of a host material, an emitting dopant, and an assisting dopant.

As a host material forming the base material of the light emitting layer 5, an organic compound such as CBP expressed by the formula (3) above is employed.

It is desirable that the emitting dopant is composed of an organic material emitting red light. For example, a singlet organic material, such as (2-(1,1-dimethylethyl)-6-(2-(2,3,6,7-tetrahydro-1,1,7,7-tetramethyl-1II,5II-benzo[ij]quinolizine-9-yl)ethenyl)-4H-pyran-4-ylidene)propandinitril (hereinafter abbreviated as DCJTB) expressed by the following formula (25) or a triplet organic material, such as bis(2-2'-benzothienyl)-pyridinato-N,C3iridium(acetylacetonate) (hereinafter abbreviated as btp2Ir(acac)) expressed by the following formula (26) or iridium(III)tris(2-naphthalene-1-yl-quinolinato)-N,$C^2$ (hereinafter abbreviated as Ir(Naphq)$_3$) expressed by the following formula (27) are mentioned.

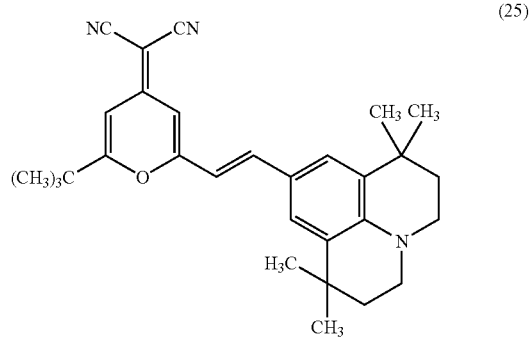
(25)

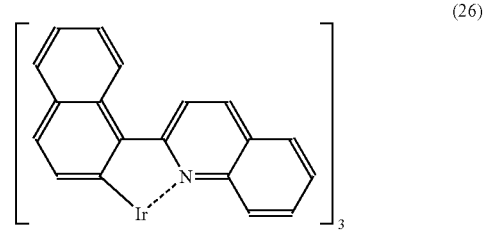
(26)

-continued

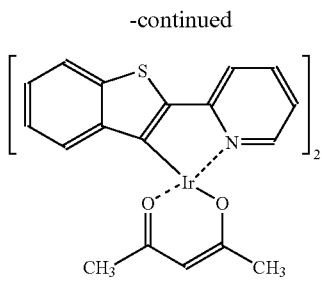

(27)

Note that the singlet organic material herein represents an organic material which can convert singlet excitation energy into a light emission, while the triplet organic material represents an organic material which can convert triplet excitation energy into a light emission.

The assisting dopant serves to transfer the energy excited by the above host material to the emitting dopant. In the present embodiment, the compound for light emitting device according to any of the above first to fifth embodiments is employed as the assisting dopant. In the present embodiment, it is preferable that the assisting dopant made of the above-described compound for light emitting device emits orange-red light in the case where the emitting dopant emits red light.

The luminescent wavelength of the emitting dopant is longer than that of the host material. In the case where the interval between the luminescent wavelength of the host material and the luminescent wavelength of the emitting dopant is short, the excitation energy generated by the host material is effectively transferred to the emitting dopant.

However, in the case where the interval between the luminescent wavelength of the host material and that of the emitting dopant is long, it is difficult to transfer the excitation energy generated by the host material to the emitting dopant.

For this reason, the assisting dopant having a luminescent wavelength is doped between the luminescent wavelength of the host material and the luminescent wavelength of the emitting dopant, so that the assisting dopant acts as a bridge to transfer the excitation energy generated in the host material to the emitting dopant. This results in a satisfactory emission from the emitting dopant and improved luminous efficiency of the organic EL device itself.

As described above, the organic EL device according to the present embodiment provides improved luminous intensity of the emitting dopant and improved luminous efficiency, through the employment of the compound for light emitting device as the assisting dopant, even if the compound for light emitting device is not emitted.

Seventh Embodiment

An organic EL device according to a seventh embodiment has a similar structure as that of the organic EL device according to the first embodiment except that the compound for light emitting device according to any of the first to fifth embodiments is employed as a hole blocking layer 6.

The compound for light emitting device has electron transport capability, as mentioned above. By the employment of this compound for light emitting device as the hole blocking layer 6, electrons are transported, while holes are prevented from being transferred.

In general, a hole blocking layer 6 made of an organic material without electron transport capability, is formed with a small thickness in order to transfer electrons. However, as for the hole blocking layer 6 in the present embodiment, the layer can be formed with a large thickness, by the employment of the compound for light emitting device with electron transport capability.

Accordingly, the hole blocking layer 6 can be formed with a large thickness, resulting in the fabrication of an organic EL device having high yield. A highly reliable organic EL device is thus fabricated.

Moreover, because the formation of the hole blocking layer 6 with a large thickness is allowed, it is not necessary to make precise adjustments to the thickness, thus leading to improved productivity.

EXAMPLES

Organic EL devices in Inventive Example 1, Comparative Example 1, and Comparative Example 2 were fabricated based on the embodiments of the present invention, and drive voltage was applied to each of the fabricated organic EL devices to measure luminescent characteristics.

Inventive Example 1

The organic EL device in Inventive Example 1 has a similar structure as that of the organic EL device in the above first embodiment. In the organic EL device in Inventive Example 1, a glass substrate was employed as the substrate 1, and ITO was employed as the hole injection electrode 2. In addition, CuPc (with a thickness of 100 Å) was employed as the hole injection layer 3, NPB (with a thickness of 500 Å) was employed as the hole transport layer 4, and CPB and the compound HD1 for light emitting device in the above first embodiment were employed as the light emitting layer 5. The light emitting layer 5 was 250 Å in thickness. Moreover, BAlq (with a thickness of 100 Å) was employed as the hole blocking layer 6, Alq (with a thickness of 400 Å) was employed as the electron injection layer 7, and a cathode electrode (with a thickness of 2000 Å) made of lithium fluoride and aluminum was employed as the electron injection electrode 8.

As for the light emitting layer 5, the CBP was employed as a host material, and the compound HD1 for light emitting device as an emitting dopant. The compound HD1 for light emitting device was doped in an amount of 6.5% by weight for the light emitting layer 5.

The organic EL device in Inventive Example 1 was fabricated as follows.

First, the substrate 1 (glass substrate) already provided with the hole injection electrode 2 (ITO) was twice subjected to ultrasonic cleaning in isopropyl alcohol for five minutes, and the surfaces of the substrate 1 and the hole injection electrode 2 were washed by an ozone cleaner.

After that, the hole injection layer 3 (CuPc), hole transport layer 4 (NPB), light emitting layer 5 (CBP and compound HD1 for light emitting device), hole blocking layer 6 (BAlq), electron injection layer 7 (Alq), and electron injection electrode 8 (lithium fluoride and aluminum) were sequentially deposited on the hole injection electrode 2 (ITO) by vacuum evaporation.

Vapor deposition of each of the layers forming the organic EL device was performed at a vacuum degree of $1 \times 10^{-6}$ Torr without controlling the temperature.

Description will now be made of a process of preparing the compound HD1 for light emitting device employed in the light emitting layer 5. The compound HD1 for light emitting device was prepared similarly as in the first embodiment.

In a three-neck flask (200 ml) with a reflux tube, 2-[4-(dimesitylboryl)phenyl]pyridine KA1 expressed by the above formula (11): 3.22 g (8.00 mmol), iridium trichloride (III) n hydrate ($IrCl_3 \cdot nH_2O$): 0.600 g (2.00 mmol), 2-ethoxyethanol: 60 ml, and water: 20 ml were mixed. The mixture was then stirred under reflux in a nitrogen atmosphere for 24 hours. A resultant reactance was cooled to the room temperature, and subsequently a precipitated solid was filtered. The filtered solid was washed in water and ethanol, and dried under reduced pressure to give a 1.26 g yellow powder of the compound TU1 for light emitting device (with a yield of 61%) expressed by the above formula (12).

After that, in a three-neck flask (200 ml) with a reflux tube, the compound TU1: 0.414 g (0.200 mmol), picolinic acid KA2 expressed by the above formula (13): 00.61 g (0.513 mmol), 2-ethoxyethanol: 20 ml, and sodium carbonate ($Na_2CO_3$): 0.25 g were mixed, and the mixture was stirred under reflux in a nitrogen atmosphere for 15 hours. A resultant reactance was cooled to the room temperature, and subsequently a precipitated solid was filtered. The filtered solid was washed in water and ethanol, dried under reduced pressure, and then purified using silica gel column chromatography (eluting solvent: dichloromethane) to give a 0.301 g yellow powder of the compound HD1 for light emitting device (with a yield of 67%). The compound HD1 for light emitting device was thus prepared.

The organic EL device thus prepared was biased such that the hole injection electrode 2 was positive, and the electron injection electrode 8 was negative to measure the luminescent characteristics.

As a result, an orange emission with a maximum luminescent wavelength of 580 nm was attained. The full width at half-maximum of the emission spectrum was 70 nm.

Comparative Example 1

The organic EL device in Comparative Example 1 has a similar structure as that of the organic EL device in Inventive Example 1 except that a different compound for light emitting device was employed for the emitting dopant of light emitting layer 5.

As the emitting dopant in Comparative Example 1, iridium(III)bis(2-phenylbenzothiazolato)-N, $C^2$-acetylacetonate (hereinafter abbreviated as $(bt)_2Ir(acac)$) (disclosed in "S. Lamansky, et al, J. Am. Chem. Soc. 2001, 123, 4304.") expressed by the following formula (28) was employed:

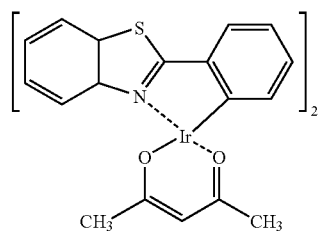

(28)

The organic EL device thus prepared was biased such that the hole injection electrode 2 was positive, and the electron injection electrode 8 was negative to measure the luminescent characteristics.

As a result, an orange emission with a maximum luminescent wavelength of 558 nm was attained. The full width at half-maximum of the emission spectrum was 100 nm.

Comparative Example 2

The organic EL device in Comparative Example 2 has a similar structure as that of the organic EL device in Inventive Example 1 except that a different compound for light emitting device was employed for the emitting dopant of light emitting layer 5.

As the emitting dopant in Comparative Example 2, iridium(III)tris(2-phenylpyridinato)-N,$C^2$ (hereinafter abbreviated as Ir(ppy)3) expressed by the following formula (4) was employed:

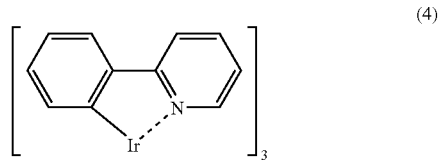

(4)

The organic EL device thus prepared was biased such that the hole injection electrode 2 was positive, and the electron injection electrode 8 was negative to measure the luminescent characteristics.

As a result, a green emission with a maximum luminescent wavelength of 515 nm was attained. The full width at half-maximum of the emission spectrum was 60 nm.

(Evaluation)

From the measurement results of the luminescent characteristics of the organic EL devices in Inventive Example 1, Comparative Examples 1, 2, Inventive Example 1 and Comparative Example 1 were compared, and Inventive Example 1 and Comparative Example 2 were compared. Table 1 below shows the maximum luminescent wavelengths and full widths at half-maximum of Inventive Example 1, Comparative Example 1 and Comparative Example 2.

TABLE 1

| organic EL device | emitting dopant | maximum luminescent wavelength (nm) | full width at half-maximum (nm) |
|---|---|---|---|
| organic EL device in Inventive Example 1 | compound HD1 for light emitting device | 580 | 70 |
| organic EL device in Comparative Example 1 | $(bt)_2Ir(acac)$ | 558 | 100 |
| organic EL device in Comparative Example 2 | $Ir(ppy)_3$ | 515 | 60 |

Figure 7:
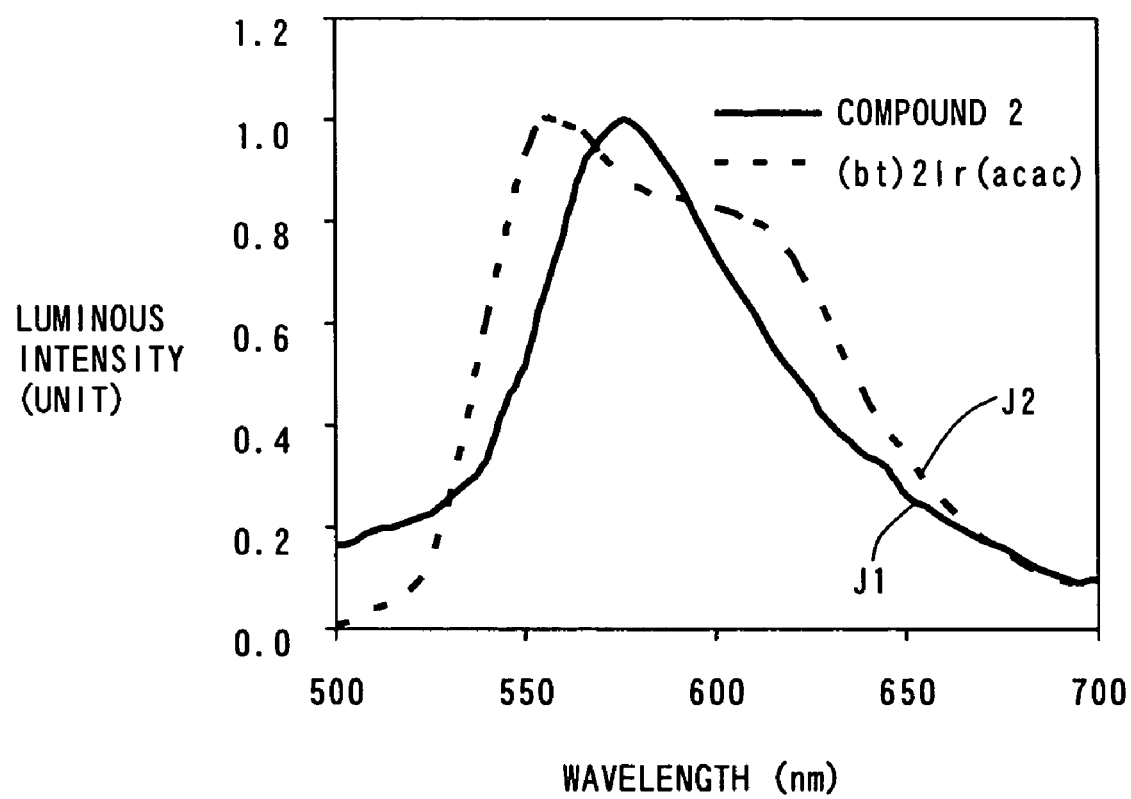
FIG. 7 is a graph showing the luminescent characteristics obtained in Inventive Example 1 and Comparative Example 1.

FIG. 7 is a graph showing the luminescent characteristics obtained in Inventive Example 1 and Comparative Example 1. The ordinate shows luminous intensity, and the abscissa shows luminescent wavelength. The solid line J1 represents the luminescent characteristics of the organic EL device in Inventive Example 1, whereas the solid line J2 represents the luminescent characteristics of the organic EL device in Comparative Example 1.

With reference to Table 1 and FIG. 7, the maximum luminescent wavelength of Inventive Example 1 is located at a longer wavelength than those of Comparative Examples 1 and 2. When the maximum luminescent wavelength is shifted to a longer wavelength as in this case, an orange emission of good purity is attained.

In addition, the full width at half-maximum of Inventive Example 1 is smaller than that of Comparative Example 1, and it is almost equal to that of Comparative Example 2. When the full width at half-maximum of the emission spectrum is small as in this case, a sufficient emission in a visible light range can be made.

Consequently, it was made clear that the organic EL device employing the emitting dopant into which a substituent containing boron is introduced provides excellent color purity and excellent luminous efficiency.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A compound for light emitting device having a molecular structure expressed by the following formula (1):

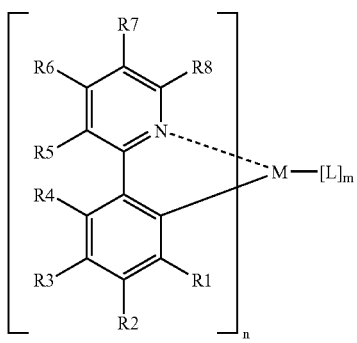

wherein at least one out of R1 to R8 is a substituent containing boron; the others are each a hydrogen atom or a substituent; L is a ligand; M is a metal; m represents an integer from 0 to 4; n represents an integer from 1 to 3; and said substituent containing boron is expressed by the following formula (2):

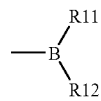

wherein R11 and R12 are identical to or different from each other, each being a hydrogen atom or a substituent.

2. The compound for light emitting device according to claim 1, wherein said R11 and R12 are each a mesityl group.

3. The compound for light emitting device according to claim 1, wherein
said L is a ligand selected from the group consisting of a halogen ligand, a carboxylic acid ligand, an imine ligand, a nitrogen-containing heterocyclic ligand, a diketone ligand, a phosphorus ligand, an isocyanide ligand, an ortho carbometallation ligand, a hexafluorophosphine ligand, a cyclopentadienyl ligand, and a carbon monoxide ligand.

4. The compound for light emitting device according to claim 1, wherein
said L is a ligand selected from the group consisting of a picolinic acid ligand, a salicylic acid ligand, a salicylimine ligand, an acetylacetone ligand, and an ortho carbometallation ligand.

5. The compound for light emitting device according to claim 1, wherein
said M is a metal selected from the group consisting of iridium, platinum, palladium, rhodium, and rhenium.

6. The compound for light emitting device according to claim 1, wherein said R1 and R3 to R8 are each a hydrogen atom.

7. An organic light emitting device comprising:
a hole injection electrode;
an electron injection electrode;
a light emitting layer provided between said hole injection electrode and said electron injection electrode, wherein said light emitting layer contains an organic compound having a molecular structure expressed by the following formula (1):

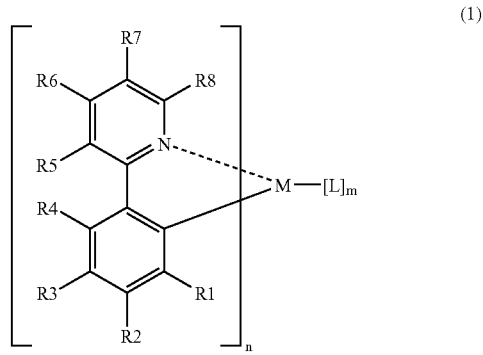

wherein at least one out of R1 to R8 is a substituent containing boron; the others are each a hydrogen atom or a substituent; L is a ligand; M is a metal; m represents an integer from 0 to 4; n represents an integer from 1 to 3; and said light emitting layer contains a host material and said organic compound expressed by said formula (1), the content of said organic compound being not less than 0.1% nor more than 30% by weight of said host material.

8. The organic light emitting device according to claim 7, wherein
said host material is 4,4'-N,N'-dicarbazole-1,1'-biphenyl having a molecular structure expressed by the following formula (3)

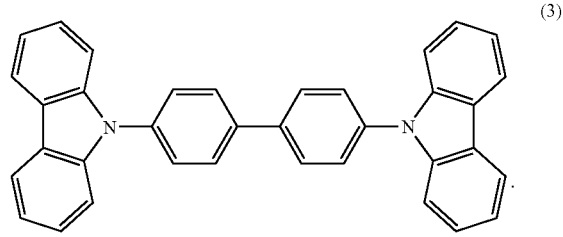

9. An organic light emitting device comprising:
a hole injection electrode;
an electron injection electrode;
a carrier transport layer provided between said hole injection electrode and said electron injection electrode; and
a light emitting layer provided between said hole injection electrode and said electron injection electrode, wherein at least one of said carrier transport layer and said light emitting layer contains an organic compound having a molecular structure expressed by the following formula (1):

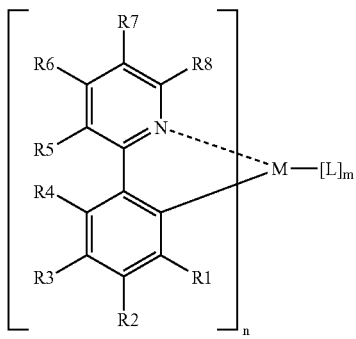
(1)

wherein at least one out of R1 to R8 is a substituent containing boron; the others are each a hydrogen atom or a substituent; L is a ligand; M is a metal; m represents an integer from 0 to 4; n represents an integer from 1 to 3 and said substituent containing boron is expressed by the following formula (2):

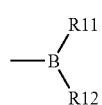
(2)

wherein R11 and R12 are identical to or different from each other, each being a hydrogen atom or a substituent.

* * * * *